United States Patent
Stevens

(10) Patent No.: US 9,903,845 B2
(45) Date of Patent: Feb. 27, 2018

(54) IONIZATION OF ANALYTE MOLECULES COMPRISED IN A FLOW OF GAS

(71) Applicant: Waters Technologies Corporation, Milford, MA (US)

(72) Inventor: Douglas M. Stevens, Holden, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 0 days.

(21) Appl. No.: 14/377,259

(22) PCT Filed: Jan. 30, 2013

(86) PCT No.: PCT/US2013/023854
§ 371 (c)(1),
(2) Date: Aug. 7, 2014

(87) PCT Pub. No.: WO2013/122745
PCT Pub. Date: Aug. 22, 2013

(65) Prior Publication Data
US 2015/0338384 A1    Nov. 26, 2015

Related U.S. Application Data

(60) Provisional application No. 61/597,975, filed on Feb. 13, 2012.

(51) Int. Cl.
*H01J 49/16*    (2006.01)
*G01N 30/84*    (2006.01)
(Continued)

(52) U.S. Cl.
CPC ......... *G01N 30/84* (2013.01); *G01N 30/7206* (2013.01); *H01J 27/26* (2013.01);
(Continued)

(58) Field of Classification Search
CPC ...... H01J 49/165; H01J 49/167; H01J 49/168; H01J 49/10
See application file for complete search history.

(56) References Cited

U.S. PATENT DOCUMENTS 5,572,023 A * 11/1996 Caprioli ............. G01N 30/7266
                                                       250/281
3,360,682 A    12/1997  Moore
(Continued)

FOREIGN PATENT DOCUMENTS

JP    10-112280 A    4/1998
JP    2000-106127 A    4/2000
(Continued)

OTHER PUBLICATIONS

Chan, et al.; A Combined Desorption Ionization by Charge Exchange (DICE) and Desorption Electrospray Ionization (DESI) Source for Mass Spectrometry, J. Am. Soc. Mass Spectrom (2011) 22:173-178.
(Continued)

*Primary Examiner* — Jason McCormack
*Assistant Examiner* — Sean Luck
(74) *Attorney, Agent, or Firm* — Schmeiser, Olsen & Watts LLP

(57) ABSTRACT

An apparatus for ionizing analyte molecules comprised in a flow of a first gas. The apparatus includes an inlet tube through which the first gas may be discharged into an ionization region. The apparatus also includes a nozzle electrode disposed around the inlet tube to define a substantially annular space between the exterior of the inlet tube and the interior of the nozzle electrode. The sheath tube includes an inlet for introducing a fluid into the substantially annular space and an outlet through which the fluid may be discharged into the ionization region. The apparatus is config-
(Continued)

ured to ionize the analyte molecules optionally via electrospray or chemical ionization.

16 Claims, 3 Drawing Sheets

(51) Int. Cl.
*H01J 27/26* (2006.01)
*H01J 49/04* (2006.01)
*G01N 30/72* (2006.01)
*H01J 49/14* (2006.01)

(52) U.S. Cl.
CPC .. *H01J 49/0422* (2013.01); *G01N 2030/8447* (2013.01); *H01J 49/0468* (2013.01); *H01J 49/145* (2013.01); *H01J 49/165* (2013.01)

(56) References Cited

U.S. PATENT DOCUMENTS

| | | | | |
|---|---|---|---|---|
| 5,877,495 | A * | 3/1999 | Takada | H01J 49/0431 250/288 |
| 7,091,493 | B2 | 8/2006 | Hiraoka | |
| 8,253,098 | B2 | 8/2012 | Hiraoka et al. | |
| 2004/0113068 | A1 * | 6/2004 | Bousse | B01L 3/0268 250/288 |
| 2006/0113463 | A1 * | 6/2006 | Rossier | H01J 49/167 250/288 |
| 2007/0120066 | A1 * | 5/2007 | Suzuki | H01J 49/165 250/423 R |
| 2009/0194687 | A1 * | 8/2009 | Jolliffe | H01J 49/10 250/288 |
| 2009/0250608 | A1 * | 10/2009 | Mordehai | H01J 49/167 250/288 |
| 2011/0266433 | A1 | 11/2011 | Jarrell | |

FOREIGN PATENT DOCUMENTS

| | | |
|---|---|---|
| JP | 2000-214135 A | 8/2000 |
| JP | 2001-074697 A | 3/2001 |
| JP | 2004-257873 A | 9/2004 |
| JP | 2011-242175 A | 12/2011 |
| WO | 2006/060130 A2 | 6/2006 |
| WO | 2009/157312 A1 | 12/2009 |
| WO | 2010148339 | 12/2010 |

OTHER PUBLICATIONS

Brenner, et al.; Simple Coupling of Gas Chromatography to Electrospray Ionization Mass Spectrometry, Anal. Chem. 2008, 80, 8334-8339.
Chan, et al.; Desorption Ionization by Charge Exchange (DICE) for Sample Analysis under Ambient Conditions by Mass Spectrometry, J. Am. Soc. Mass Spectrom 2010, 21, 1554-1560.
Lloyd, et al.; A Corona Discharge Initiated Electrochemical Electrospray Ionization Technique, J. Am. Soc. Mass Spectrom 2009, 20, 1988-1996.
Yang, et al.; Aliphatic Hydrocarbon Spectra by Helium Ionization Mass Spectrometry (HIMS) on a Modified Atmospheric-Pressure Source Designed for Electrospray Ionization, J. Am. Soc. Mass Spectrom (2011) 11:1395-1402.
International Search Report for Application No. PCT/US2013/023854, filed Jan. 30, 2013, 4 pages.
International Written Opinion Report for Application No. PCT/US2013/023854, filed Jan. 30, 2013, 5 pages.
Extended Euorpean Search Report for Application No. 13748840.9, dated Aug. 27, 2015 (7 pages).
Japanese Search Report for Application No. 2014-556574, dated Aug. 24, 2016 (45 pages).
Japanese Office Action for Application No. 2014-556574, dated Aug. 30, 2016 (7 pages).

* cited by examiner

IONIZATION OF ANALYTE MOLECULES COMPRISED IN A FLOW OF GAS

RELATED APPLICATIONS

This application is the National Stage of International Application No. PCT/US2013/023854, filed on Jan. 30, 2013, which claims priority to and benefit of U.S. Provisional Patent Application No. 61/597,975 entitled "Ionization Of Analyte Molecules Comprised In A Flow of Gas," filed Feb. 13, 2012. The contents and teachings of each of these applications are hereby expressly incorporated herein by reference in their entirety.

TECHNICAL FIELD

This disclosure relates to ionization of analyte molecules comprised in a flow of gas.

BACKGROUND

In gas chromatography, a flow of a mobile phase gas (or "carrier gas"), typically an inert gas, sweeps a sample through a gas chromatography (GC) column. Generally, the GC column includes a layer of polymer or liquid that acts as a stationary phase. The sample is separated into its constituent parts (i.e., separate compounds) as it passes through the column and interacts with the stationary phase material. As a result, the various compounds that make up the sample elute from the column at different times. Often, the effluent from the column is exposed to an ionization source to ionize analyte molecules in the effluent so that ionized analyte molecules can then be detected.

SUMMARY

This disclosure is based, in part, on the realization that a nozzle electrode can be arranged near the outlet of chromatography column and configured such that analyte molecules in a flow of gas, such as the effluent from a gas chromatography column, can be ionized by electrospray or chemical ionization techniques.

One aspect provides an apparatus for ionizing analyte molecules comprised in a flow of a first gas. The apparatus includes an inlet tube through which the first gas may be discharged into an ionization region. The apparatus also includes a nozzle electrode disposed around the inlet tube to define a substantially annular space between the exterior of the inlet tube and the interior of the nozzle electrode. The sheath tube includes an inlet for introducing a fluid into the substantially annular space and an outlet through which the fluid may be discharged into the ionization region. The apparatus is configured to ionize the analyte molecules optionally via electrospray or chemical ionization.

Another aspect features a method of ionizing analyte molecules comprised in a flow of a first gas. The method includes passing the first gas through an inlet tube into an ionization region; passing a fluid (a second gas or a liquid) through a substantially annular space between the exterior of the inlet tube and the interior of a nozzle electrode such that the fluid is discharged toward the ionization region; and ionizing at least some of the analyte molecules in the ionization region via electrospray or chemical ionization.

Implementations may include one or more of the following features.

In some implementations, the inlet tube and the nozzle electrode are concentrically disposed about an axis such that a flow of the first gas and a flow of the fluid are coaxial.

In certain implementations, the first gas is discharged into the ionization region at approximately atmospheric pressure.

In some implementations, the nozzle electrode is configured to provide a corona discharge so that the analyte molecules may be ionized by chemical ionization.

In certain cases, the apparatus also includes a gas chromatography column, and the flow of the first gas includes effluent from the chromatography column.

In some implementations, the apparatus includes a heated transfer line for heating the flow of the first gas within the inlet tube.

In certain implementations, the apparatus includes a mass spectrometer having an entrance orifice disposed to receive ions formed in the ionization region.

In some examples, the entrance orifice is arranged to be coaxial with the flow of the first gas exiting the inlet tube.

In certain examples, the apparatus includes a reaction chamber disposed between the nozzle electrode and the mass spectrometer for enclosing the ionization region.

In some implementations, the fluid comprises a second gas (e.g., nitrogen), and the analyte molecules are ionized by chemical ionization using a corona discharge provided via the nozzle electrode.

In certain implementations, the fluid is a liquid that is vaporized as it is passed through the nozzle electrode, and the analyte molecules are ionized by chemical ionization using a corona discharge provided via the nozzle electrode.

In some cases, the analyte molecules are ionized by electrospray ionization via the nozzle electrode.

In some implementations, the first gas is passed through a chromatography column, and passing the first gas through the inlet tube includes passing the effluent from the chromatography column through the inlet tube.

In certain implementations, ions generated in the ionization region are passed into a mass spectrometer for mass analysis.

In some examples, the ions generates in the ionization region are passed towards a collector electrode to perform non-mass spectrometric detection of the generated ions.

In certain examples, flows of the first gas and the fluid are discharged into the ionization region coaxially.

Implementations can provide one or more of the following advantages.

Some implementations allow electrospray ionization to be used for ionizing analyte molecules in a flow of gas.

Implementations can provide the flexibility of applying either electrospray or chemical ionization techniques for ionizing analyte molecules comprised in a flow of gas.

Certain implementations provide sensitivity and selectivity differences as compared to known atmospheric pressure chemical ionization (APCI) techniques.

The introduction of liquid for electrospray ionization can be decoupled from chromatography. Consequently, the polarity, pH, and salt content of a liquid used for electrospray ionization may be varied to adjust selectivity and sensitivity of the ionization.

Other aspects, features, and advantages are in the description, drawings, and claims.

BRIEF DESCRIPTION OF THE DRAWINGS

Like reference numbers indicate like elements.

DETAILED DESCRIPTION

Figure 1:
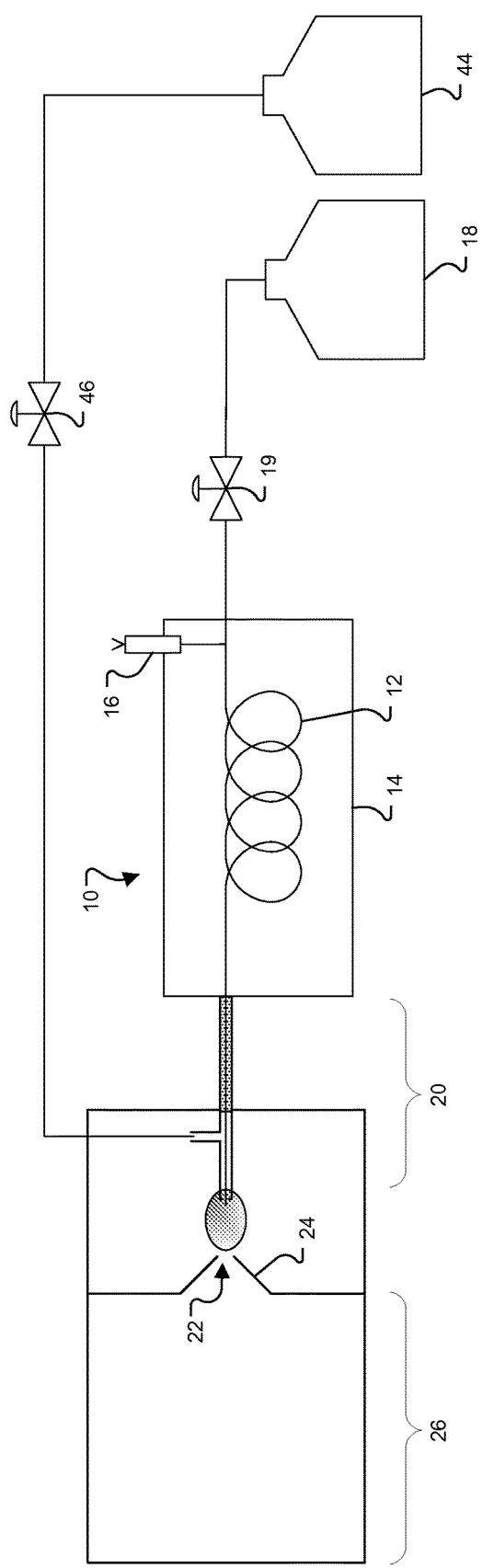
FIG. 1 is a schematic view of a gas chromatography/mass spectrometry (GC/MS) instrument.

Referring to FIG. 1, a gas chromatograph 10 includes a gas chromatography (GC) column 12 inside a temperature controlled oven 14. A sample is introduced on to the GC column 12 through a sample injector 16 into a flow of a first fluid (carrier gas) from a first reservoir 18. A first flow controller 19 is provided to maintain a constant flow of the carrier gas (mobile phase), which may be nitrogen ($N_2$) or helium (He) gas. A flow of about 0.5 ml/minute to about 10 ml/minute (e.g., about 1 ml/minute) would be suitable for many capillary GC columns. The GC column 12 is a coil of metal, glass, or fused silica capillary tubing, typically 0.53 mm or smaller internal diameter and 0.8 mm or smaller outside diameter, internally coated with a stationary phase suitable for effecting separation of different chemical components of the sample. The effluent from the GC column 12, including analyte molecules in a flow of the carrier gas at a pressure approximately equal to atmospheric pressure (e.g., about 980 millibars (mb) to about 1050 mb), passes into an interface device generally indicated at 20. Ionized analyte molecules emerge from the interface device 20 and are sampled through a small orifice 22 in a sampling cone 24 of a mass spectrometer generally indicated by 26.

Figure 2:
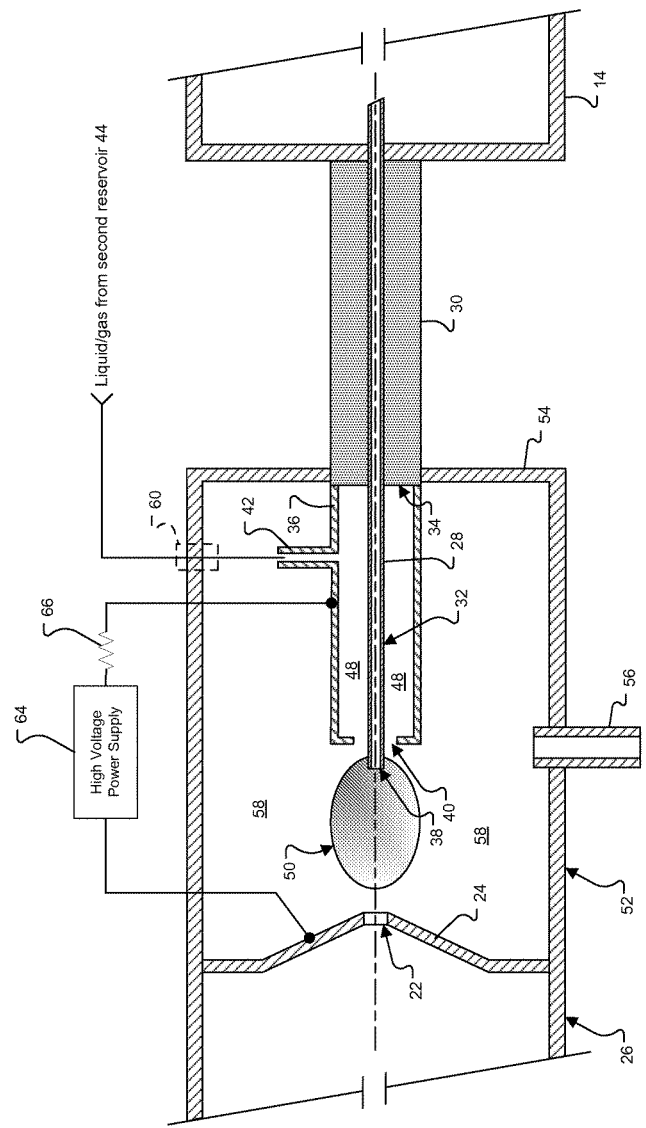
FIG. 2 is a detailed view of one arrangement of part of the instrument shown in FIG. 1.

An implementation of the interface device 20 is shown in FIG. 2. An inlet tube 28 is either integral with, or is connected to, the outlet of the GC column 12. For example, the inlet tube 28 may be a distal end portion of the GC column 12. Alternatively, the inlet tube 28 may be a fused silica tube connected to the distal (outlet) end of the GC column 12. The inlet tube 28 extends through a wall of the oven 14 towards the sampling cone 24 of the mass spectrometer 26. The inlet tube 28 passes through a heated transfer line 30, which circumferentially surrounds a portion of the inlet tube 28. The transfer line 30 can include a tube of thermally conductive material, such as a metal or metal alloy, e.g., stainless steel, surrounded by a heater, such as a coiled resistance wire or tape heater. The transfer line 30 is capable of maintaining the temperature of the inlet tube 28 sufficiently high to prevent loss of analyte molecules as they travel through the inlet tube 28. The necessary temperature is dependent on the nature of the analyte molecules, but may typically be in the range 100° C.-300° C.

A distal end portion 32 of the inlet tube 28 extends beyond the distal end 34 of the transfer line 30 and into a nozzle electrode 36. The nozzle electrode 36 has a generally cylindrical shape and is formed of an electrically conductive material such as a metal or metal alloy, e.g., stainless steel. The nozzle electrode 36 circumferentially surrounds the inlet tube 28 with the distal (outlet) end 38 of the inlet tube 28 extending outwardly from an outlet 40 of the nozzle electrode 36. The nozzle electrode 36 can be electrically isolated from the transfer line 30. For example, in some cases a threaded ceramic insulator which screws into the distal end 34 of the transfer line 30 and into which the nozzle electrode 36 screws can provide for electrical isolation. Both the inlet tube 28 and the nozzle electrode 36 can have circular cross sections and are concentrically disposed. However, any cross-sectional shapes can be used.

The nozzle electrode 36 includes a fluid inlet 42. A supply of a second fluid (e.g., a liquid, such as methanol, or a gas, such as nitrogen) from a second reservoir 44 (FIG. 1) is connected to the fluid inlet 42 via a second flow controller 46 (FIG. 1). The second fluid flows, coaxially to the flow of the GC column effluent, in the annular space 48 between the inside of the nozzle electrode 36 and the exterior of the inlet tube 28. The second fluid exits through the outlet 40 of the nozzle electrode 36 and merges with the effluent exiting the inlet tube 28 in an ionization region 50 where the analyte molecules are ionized.

A reaction chamber 52 including a housing 54 and a vent 56 surrounds the ionization region 50. The vent 56 discharges to atmospheric pressure so that the pressure in the inner volume 58 of the housing 54 is substantially equal to atmospheric pressure. Some implementations may include a variable flow restrictor or a pump connected to the vent 56 for controlling pressure and/or gas concentration in the reaction chamber 52. The distal end 34 of the transfer line 30 is mounted through a wall of the housing 54 such that the nozzle electrode 36 is enclosed within the inner volume 58. The housing 54 can be formed of a metal or metal alloy. Fluidic connection between the nozzle electrode 36 and the second reservoir 44 (FIG. 1) can be established via a feedthrough 60 in the housing 54.

Ionization may be effected through electrospray or a corona discharge established by application of a suitable electrical potential difference between the nozzle electrode 36 and at least the sampling cone 24 of the mass spectrometer 26. In this regard, a power supply 64 connected to the nozzle electrode 36 via a current limiting resistor 66 may be employed to provide this potential difference. The power supply 64 can apply a high voltage of about 2000 Volts to about 5000 Volts to the nozzle electrode 36 to promote ionization.

Analyte molecules present in the ionization region 50 are ionized through electrospray ionization or chemical ionization techniques (e.g., charge exchange, protonation, and deprotonation). The ionization technique can be controlled, at least in part, based on the type of fluid that is introduced in the nozzle electrode 36 through the fluid inlet 42. And, since the second fluid is effectively decoupled from the chromatography, either a gas or a liquid can be used. For example, ionization via a chemical ionization technique can be achieved by introducing a gas, such as $N_2$, into the fluid inlet 42 of the nozzle electrode 36. In this case, the applied voltage allows the nozzle electrode 36 to take the place of a corona pin as a discharge electrode providing a corona discharge in the ionization region 50 to promote ionization by charge exchange. Charge exchange chemical ionization can be beneficial for analyzing less polar analytes.

Alternatively, a liquid, such as methanol, could support protonation or electrospray ionization depending on how much of the liquid is introduced. For example, if only a trickle of methanol is provided it may vaporize before exiting the nozzle electrode 36 and proton transfer may be initiated by a corona discharge provided by the nozzle electrode 36 acting as a corona pin. On the other hand, a sustained electrospray may be supported if a relatively large amount of liquid methanol is introduced into the nozzle electrode 36 such that the liquid, upon reaching the outlet 40 of the nozzle electrode 36, forms a Taylor cone. Electrospray ionization can be beneficial when analyzing high polar analytes by providing a selectively higher response. Since the second fluid is effectively decoupled from the chromatography, the polarity of the liquid, pH, and salt content can be varied to alter the selectivity and sensitivity of the ionization.

Ions generated in the ionization region 50 by electrospray or chemical ionization flow into the mass spectrometer 26 induced by the combined effects of electrostatic attraction and vacuum. The ions pass through the orifice 22 in the sampling cone 24 and are subsequently analyzed by the mass spectrometer 26.

Other Implementations

Although a few implementations have been described in detail above, other modifications are possible. For example, while an implementation has been described in which the distal end of the inlet tube extends beyond the outlet of the nozzle electrode, in some implementations, the distal end of the inlet tube may instead be substantially aligned with the outlet of the nozzle electrode or refracted within the nozzle electrode.

Figure 3:
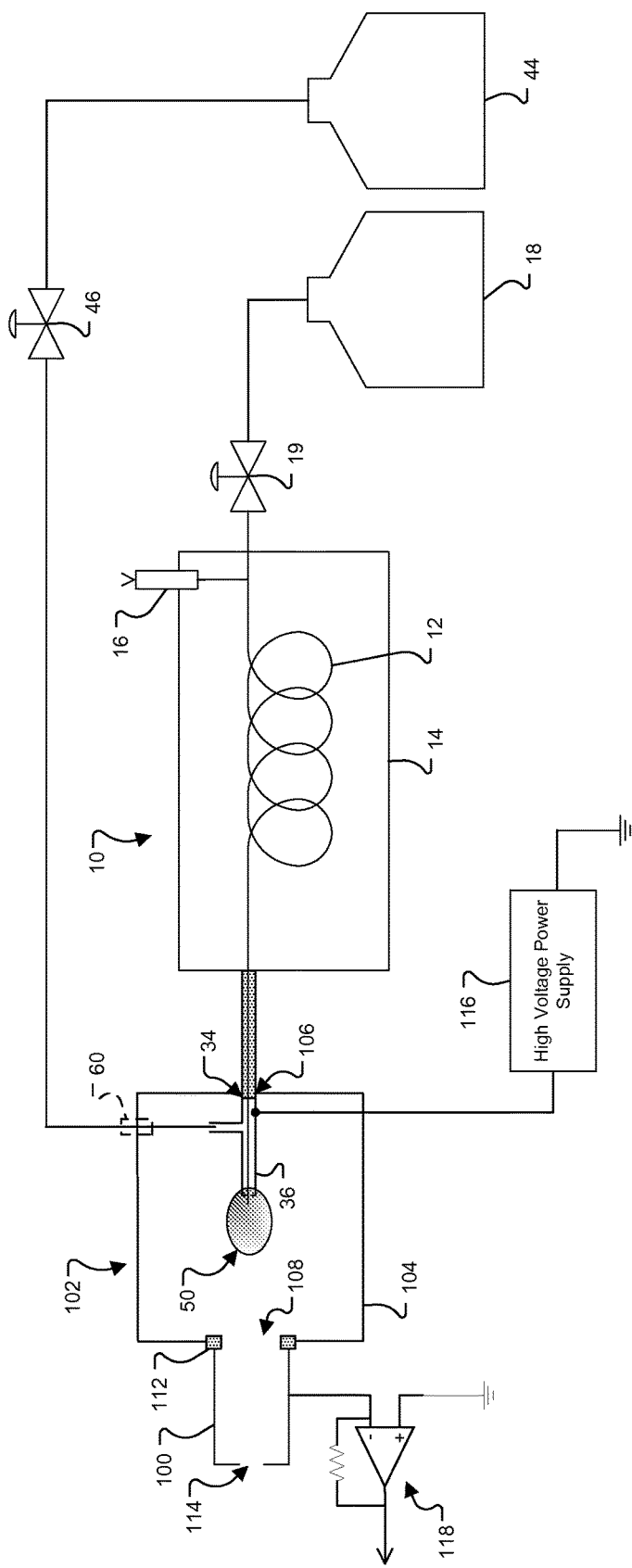
FIG. 3 is a schematic view of a gas chromatography instrument including a collector electrode arrangement for detecting analyte ions.

Although implementations have been described in which analyte ions are detected using a mass spectrometer, in some implementations, a non-mass spectrometric detector may be used for detecting the analyte ions. FIG. 3 illustrates an implementation that utilizes a collector electrode 100 for detecting a total current of ions formed, rather than individual ion intensities as in mass spectrometry. As shown in FIG. 3, a reaction chamber 102 is provided to contain the ionization region 50. The reaction chamber 102 includes a housing 104 that defines an inlet 106 and an outlet 108 and can be formed of a metal or metal alloy. The distal end 34 of the transfer line 30 is mounted through the inlet 106 of the housing 104 such that the nozzle electrode 36 is substantially enclosed within the housing 104. Again, fluidic connection between the nozzle electrode 36 and the second reservoir 44 can be established via a feedthrough 60 in the housing 54.

The collector electrode 100 is a cylindrical electrode formed of an electrically conductive material such as a metal or metal alloy, e.g., stainless steel. The collector electrode 100 is mounted adjacent the outlet 108 of the reaction chamber 102. An insulator 112 can be positioned between the collector electrode 100 and the reaction chamber 102 to electrically isolate the collector electrode 100. The collector electrode 100 is configured to attract ions from the reaction chamber 102 for detection. The collector electrode 100 also includes an exhaust 114 for venting remaining gases, including neutral species and ions having polarity that is the same as that of the collector electrode 100. Some implementations may include a variable flow restrictor or a pump disposed at the exhaust 114 of the collector electrode 100 for controlling pressure and/or gas concentration in the reaction chamber 102.

A power supply 116 is connected to the nozzle electrode 36 for providing a high voltage (e.g., about 5 kV) and an applied current of about 0.5 μA to about 50 μA (e.g., about 2 μA to about 5 μA) thereto. The power supply 116 can be a high voltage power supply (e.g., 6 kV, 50 μA) capable of reversing the output polarity (e.g., within milliseconds).

In some cases, the collector electrode 100 can be electrically connected to the inverting input of a virtual ground 118. The virtual ground 118 can be provided by a current amplifier, such as the Model 428 current amplifier available from Keithley Instruments, Inc., Cleveland, Ohio. The output of the virtual ground can be connected to a voltage monitoring instrument (e.g., an A/D converter), which, in turn, can provide a corresponding signal to a computing system for analysis and display.

While an implementation has been described in which an ionization region is enclosed within a reaction chamber, in some implementation, the nozzle electrode output may merely be positioned to provide an ionization region adjacent to an inlet of a mass spectrometer in the absence of a reaction chamber.

In some implementations, the respective polarities of the nozzle electrode and the cone are switched rapidly (e.g., every 20 milliseconds or a 50 Hz switching frequency), which can allow for the detection of a wider range of analytes.

Although implementations have been described in which an interface device is employed for ionizing effluent from a gas chromatography column. The interface devices described herein may similarly be employed for ionizing effluent from a super critical fluid chromatography (SFC) source. In such cases, the inlet tube can be connected to, or may be an integral part of, an SFC source such that analyte molecules in effluent from the SFC source are ionized by electrospray or chemical ionization before they are introduced into a mass spectrometer or collector electrode for detection.

Accordingly, other implementations are within the scope of the following claims.

What is claimed is:

1. An apparatus for ionizing analyte molecules comprised in a flow of a first gas, the apparatus comprising:
    an inlet tube through which the first gas may be discharged into an ionization region; and
    a nozzle electrode disposed around the inlet tube to define a substantially annular space between the exterior of the inlet tube and the interior of the nozzle electrode, the nozzle electrode comprising an inlet for introducing a liquid into the substantially annular space and an outlet through which the liquid may be discharged into the ionization region to form a Taylor cone,
    wherein the apparatus is configured to ionize the analyte molecules via electrospray ionization and wherein a distal end of the inlet tube extends beyond the outlet of the nozzle electrode into the ionization region.

2. The apparatus of claim 1, wherein the inlet tube and the nozzle electrode are concentrically disposed about an axis such that a flow of the first gas and a flow of the liquid are coaxial.

3. The apparatus of claim 1, wherein the first gas is discharged into the ionization region at approximately atmospheric pressure.

4. The apparatus of claim 1, further comprising a gas chromatography column, and wherein said flow of a first gas comprises effluent from the chromatography column.

5. The apparatus of claim 1, further comprising a heated transfer line for heating the flow of the first gas within the inlet tube.

6. The apparatus of claim 1, further comprising a mass spectrometer having an entrance orifice disposed to receive ions formed in the ionization region.

7. The apparatus of claim 6, wherein the entrance orifice is arranged to be coaxial with the flow of the first gas exiting the inlet tube.

8. The apparatus of claim 6, further comprising a reaction chamber disposed between the nozzle electrode and the mass spectrometer for enclosing the ionization region.

9. A method of ionizing analyte molecules comprised in a flow of a first gas, the method comprising:
    passing the first gas through an inlet tube such that the first gas is discharged from a distal end of the inlet tube in an ionization region;

passing a liquid through a substantially annular space between the exterior of the inlet tube and the interior of a nozzle electrode such that the liquid is discharged toward the ionization region and forms a Taylor cone, wherein the liquid is discharged from the substantially annular space at a location proximal to a distal end of the inlet tube; and ionizing at least some of the analyte molecules in the ionization region via electrospray ionization.

10. The method of claim 9, passing the first gas through a chromatography column, and wherein passing the first gas through the inlet tube comprises passing the effluent from the chromatography column through the inlet tube.

11. The method of claim 9, further comprising passing ions generated in the ionization region into a mass spectrometer for mass analysis.

12. The method of claim 9, further comprising passing the ions generated in the ionization region towards a collector electrode to perform non-mass spectrometric detection of the generated ions.

13. The method of claim 9, wherein flows of the first gas and the liquid are discharged into the ionization region coaxially.

14. The method of claim 9, wherein the liquid comprises methanol.

15. The method of claim 9, further comprising varying any of polarity, pH, and salt content of the liquid to alter selectivity and sensitivity of ionization.

16. The apparatus of claim 1, wherein the liquid comprises methanol.

* * * * *